United States Patent [19]

Aubard et al.

[11] Patent Number: 5,021,408
[45] Date of Patent: Jun. 4, 1991

[54] HYDROCORTISONE-17-OXO-21-THIOESTERS, THEIR PREPARATION AND THEIR USES AS MEDICAMENTS

[75] Inventors: Gilbert G. Aubard, Palaiseau; Agnès G. Grouhel, Meudon; Jean-Louis Junien; Claude P. Roux, both of Paris; Diéran R. Torossian, Bourg-La-Reine, all of France

[73] Assignee: Jouveinal S.A., Paris, France

[21] Appl. No.: 71,315

[22] Filed: Jul. 9, 1987

Related U.S. Application Data

[63] Continuation of Ser. No. 794,737, Nov. 4, 1985, Pat. No. 4,933,331, which is a continuation of Ser. No. 629,975, Jul. 11, 1984, abandoned.

[30] Foreign Application Priority Data

Aug. 26, 1983 [FR] France ................... 83 13777

[51] Int. Cl.$^5$ .............................................. A61K 31/56
[52] U.S. Cl. ...................................................... 514/179
[58] Field of Search ......................................... 514/179

[56] References Cited

U.S. PATENT DOCUMENTS 4,427,671 1/1984 Torossian et al. ............. 260/397.45

Primary Examiner—Shep K. Rose
Attorney, Agent, or Firm—Cushman, Darby & Cushman

[57] ABSTRACT

3,20-dione-11$\beta$-hydroxypregn-4-ene-21-thioacetate-17-butyrate and 3,20-dione-11$\beta$-hydroxypregn-4-ene-21-thiopropionate-17-butyrate, are anti-inflamatory agents.

3 Claims, No Drawings

HYDROCORTISONE-17-OXO-21-THIOESTERS, THEIR PREPARATION AND THEIR USES AS MEDICAMENTS

This is a continuation of application Ser. No. 794,737, filed Nov. 4, 1985, now U.S. Pat. No. 4,933,331 which is a continuation of Ser. No. 629,975, filed July 11, 1984, now abandoned.

Belgian Patent No. 893,957 describes compounds of formula:

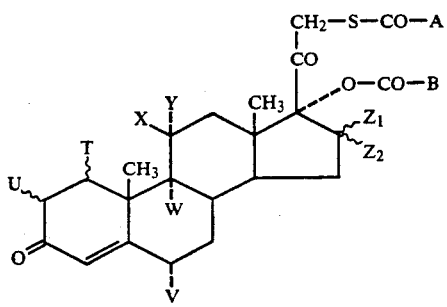

in which, independently of one another, A and B are each a straight or branched alkyl radical with 1 to 6 carbon atoms or a phenyl radical, which is optionally monosubstituted or polysubstituted by alkyl radicals having 1 to 6 carbon atoms, alkoxy having 1 to 6 carbon atoms or halogen and, independently of one another, T and U are hydrogen atoms or together form a double bond, V is a hydrogen atom or a methyl radical in the α position, W is a hydrogen atom or a halogen atom in the α position, X is a hydroxy radical in the β position and Y is a hydrogen atom or X and Y can together represent an oxygen atom, $Z_1$ is a hydrogen atom, a methyl radical in the α or β position and $Z_2$ is a hydrogen atom, or $Z_1$ and $Z_2$ together form a methylene radical.

These compounds have been found to have in some cases more than 100 times superior anti-inflammatory properties to local anti-inflammatory steroids, whose activities are recognised as being among the best of the products of this type.

However, it has now been found that among these top-quality compounds, two of them, namely 3,20-dione-11β-hydroxypregn-4-ene-21-thioacetate-17-butyrate and 3,20-dione-11β-hydroxypregn-4-ene-21-thiopropionate-17-butyrate have special and unexpected local, anti-inflammatory properties, which are much better than those of the best compounds of the aforementioned Belgian Patent.

Thus, as a selection invention, the present invention aims at the two aforementioned compounds, usable more particularly as an anti-inflammatory medicament, as well as at their preparation process.

The preparation process for the products according to the present invention essentially consists of reacting a 21-sulphonate steroid of formula:

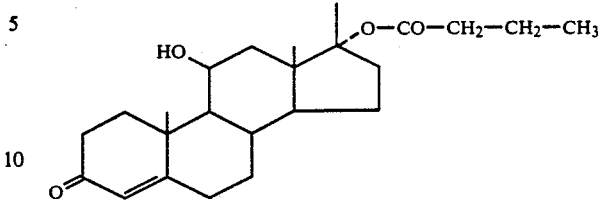

in which R corresponds to an alkyl radical, having more particularly 1 to 6 carbon atoms, with an alkali metal thiocarboxylate of formula:

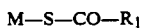

$$M—S—CO—R_1$$

in which M stands for an alkali metal atom and $R_1$ is methyl or ethyl.

These starting substances are known per se and their preparation is carried out in accordance with known processes (cf Belgian Patent No. 893,957).

The condensation reaction between these substances takes place in an appropriate aprotic solvent, such as acetone or hexametapol.

The crude product obtained is generally purified by column chromatography and then recrystallized in an alcohol, particularly a low molecular weight alcohol, to obtain a product with an appropriate purity for therapeutic use.

The purity of the products obtained is determined by per se known methods, such as thin layer chromatography, ultraviolet and infrared spectrography and elementary analysis.

For illustration purposes, in the following examples the products according to the invention are characterized by their uncorrected melting points, determined on a "Mettler FP 1" apparatus and by the main signals of their proton nuclear magnetic resonance spectra. These spectra were recorded in solution in deuterochloroform on a 60 MHz apparatus and the chemical displacements are expressed in p.p.m. relative to tetramethylsilane as the reference substance.

EXAMPLE 1

3,20-dione-11β-hydroxypregn-4-ene-21-thioacetate-17-butyrate (or hydrocortisone).

10.0 g (0.129 mole) of S-thioacetic acid and 220 ml of hexametapol are introduced into a reactor.

27.7 ml of a 4.65N sodium methylate methanolic solution (0.129 mole) are introduced, accompanied by stirring, at a temperature close to 20° C. and then the beige solution is stirred for 1 hour at ambient temperature. Within 10 minutes, a solution of 44.0 g (0.086 mole) of cortisol-21-mesylate-17-butyrate is introduced into 440 ml of hexametapol.

The solution is stirred for 2½ hours at ambient temperature. The orange solution is precipitated in 8 liters of ice water. The insoluble substances formed are filtered and then taken up in methyl ether.

The ethereal solution is extracted twice with 250 ml of 1N sodium hydroxide solution and then three times with 500 ml of saturated sodium chloride solution. After drying the ethereal phase, the solvent is eliminated by distillation.

The residue (39 g) is purified by column chromatography with the aid of 1 kg of "Florisil".

Elution by a mixture of dichloromethane and acetone 95:5 (v/v) makes it possible to collect 21 g of purified product. This product is finally recrystallized in 170 ml of a mixture of methanol and water 8:2 (v/v).

Weight = 19 g
Yield = 44.3%
Melting point = 130° C.
NMR = 1.00 (s, 18CH$_3$); 1.48 (s, 19 CH$_3$); 1.70 (m, 11$\beta$ OH); 2.35 (s, CH$_3$ ester in 21); 3.8 (s, 21CH$_2$); 4.55 (m, 11CH); 5.70 (s, 4 CH).

EXAMPLE 2

3,20-dione-11$\beta$-hydroxypregn-4-ene-21-thiopropionate-17-butyrate (or hydrocortisone).

In an identical manner to that described in example 1 and on the basis of 225 g (0.44 mole) of cortisol-21-mesylate-17-butyrate, 59.6 g (0.66 mole) of S-thiopropionic acid and 142 ml of 4.65N sodium methylate methanolic solution (0.66 mole), 200 g of purified product are obtained, which are finally recrystallized in 450 ml of methanol.

Weight = 95 g
Yield = 42.8%
Melting point = 140.5° C.
NMR = 1.00 (s, 18 CH$_3$); 1.50 (s, 19 CH$_3$); 1.70 (m, 11$\beta$ OH); 3.90 (s, 21 CH$_2$); 4.50 (m, 11 CH); 5.75 (s, 4 CH).

The powerful activity of certain steroids makes them particularly useful in the treatment of various ailments and diseases when administered by the general and/or local route. Such treatments are generally not straight forward and must be carefully carried out under medical supervision.

The anti-inflammatory activity of these structures are often accompanied by parallel secondary activities, which lead to sometimes serious and irreversible effects. The latter are usually caused by the very nature of the steroid. With respect to the class of products having a local activity, these effects and the necessary precautions in connection with their use have been frequently described, and in the recent past by A. Fritz (ann. of Allergy, Vol. 50, No.2 page 68, 1983).

Thus, the dissociation of these activities is a vital criterion for the therapeutic use of such products. Unexpectedly, the products according to the present invention have a remarkable anti-inflammatory activity, which is substantially free from side effects.

Conventional studies in man and animals have made it possible to determine the qualities of the products having a local anti-inflammatory activity.

Determination of the local anti-inflammatory activity.

In man, frequent use is made of the vasoconstriction test, which is also called the ablation test according to Mackenzie and Stoughton (Arch. Dermatol. Vol. 86, page 608, 1962). This test faithfully reflects the therapeutic activity of a product. In animals, the most frequently used tests are the cotton pellet granuloma test of C. A. Winter or Meier (J. Am. Pharm. Ass., Vol. 46, No. 9, page 515, 1957 and Experentia, Vol. 6, page 608, 1962), as well as the croton oil erythema test according to the method described by Tonelli (Endocrinology, Vol. 77, page 625, 1965). The latter test leads to results comparable to those of the vasoconstriction test (O. J. Lorenzetti - Curr. Therap. Res. Vol. 25, No. 1, page 92, 1979). Thus, in animals, it is the most representative of the therapeutic activity of a product in man.

For comparison with the vasoconstriction test, O. J. Lorenzetti and N. Bodor (reference already given and J. Med. Chem. Vol. 26, page 318, 1983) describe the results obtained with the erythema and granuloma tests. The example of hydrocortisone-17-butyrate, which is a well-known steroid marketed for its local anti-inflammatory activity (locoid) has led the Applicant to prefer the erythema test according to Tonelli for the study of the products of the present invention.

Thus, according to N. Bodor, this product only has a limited activity in the granuloma test, which places it in the class of inactive or slightly active products, whereas the results of the erythema test reported by O. J. Lorenzetti reveal a good similarity of activity compared with the vasoconstriction test.

Determination of systemic activity side effects

These effects were evaluated by means of their thymolytic activity.

The repeated administration of systemic activity products leads to a weakening of the defence systems of the organism. More especially in young animals, this leads to a reduction in the weight of two organs of the reticuloendothelial system, namely the spleen and the thymus, the latter being the most sensitive to this effect.

The results obtained by this study make it possible to calculate the activity ratio:

local anti-inflammatory activity
systemic activity the lower the figure revealed by the result obtained the more favourable and significative of a dissociation of activities.

The particularly interesting properties of the products according to the invention have been studied in comparison with the following:
hydrocortisone-21-propionate-17-butyrate
prednisolone-21-acetate-17-valerate
hydrocortisone-21-thiopivalate
prednisolone-21-thioacteate-17-valerate   6-$\alpha$-methyl-prednisolone*-21-thioacetate-17-valerate
betamethasone*-21-thiopropionate-17-acetate
betamethasone*-21-thioacetate-17-propionate
betamethasone*-21-thiopropionate-17-propionate
dexamethasone*-21-thiotertiobutylacetate-17-acetate
beclomethasone*-21-thiopropionate-17-propionate
* Products corresponding in order respectively to examples 7, 9, 10, 11, 14 and 15 of Belgian Patent No. 893,957.

In this study, hydrocortisone-21-acetate has been used as the reference substance of the present specification.

The operating protocols and the results of the pharmacological studies are given hereinafter.

In general, the compounds according to the invention, when administered to the animal by routes comparable to their insolubility properties in water, have no acute toxicity phenomena.

I - Procedures

I.1. Local anti-inflammatory activity

This study was carried out in accordance with a method derived from that of Tonelli (Endocrinology, Vol. 77, page 625, 1965).

The test consists of causing inflammation of the ear in the mouse using a croton oil-based irritating solution.

The addition of a local anti-inflammatory substance to this solution leads to a reduced inflammation action compared with that of the controls, i.e. treated with the irritating solution only.

The results of the study are expressed in $EC_{50}$, which is the p/v % concentration of the dissolved product able to bring about a 50% reduction in the inflammation compared with that caused in the controls.

I.2. Systemic activity

This activity was determined by means of a study of the activity of products on the weight reduction of the thymus of animals.

The product to be studied, suspended in 5% p/v gum arabic were orally administered daily for four consecutive days to young rats of the Wistar strain. Under the same conditions, a control batch of animals received an identical volume of the excipient.

96 hours after the first administration, the animals were killed and their thymus removed and immediately weighed.

The results of the study are expressed in $ED_{50}$, which corresponds to the daily dose in milligrams able to bring about a 50% thymus weight reduction for 1 kilogram animal weight, compared with the controls ($mg/kg^{-1}/day^{-1}$).

II. Results and comments
II.1. Results

These results for the two aforementioned tests are given in the following table I.

TABLE I

| Ref. | Studied product | Anti-inflammatory activity | | Systemic activity | |
|---|---|---|---|---|---|
| | | $EC_{50}$ % p/v | Activity/ref. 21 act. hydro | $ED_{50}$ $mg/kg^{-1}/d^{-1}$ | Activity/ref. 21 act. hydro |
| Comparison products | hydrocortisone-21-acetate | 0.30 | 1 | 14 | 1 |
| | Hydrocortisone-21-propionate-17-butyrate | 0.0047 | 63.8 | 7.2 | 1.95 |
| | Prednisolone-21-acetate-17-valerate | 0.0018 | 167 | 9.0 | 1.60 |
| | Hydrocortisone-21-thiopivalate | 2.5 | 0.12 | 3600 | 0.0038 |
| | Prednisolone-21-thioacetate-17-valerate | 0.008 | 37.5 | 58 | 0.24 |
| | 6-α-methyl-21-thioacetate-17-valerate | 0.5 | 0.6 | 43 | 0.325 |
| | Betamethasone-21-thio-propionate-17-acetate | 0.012 | 25.0 | 2.4 | 5.83 |
| | Betamethasone-21-thio-acetate-17-propionate | 0.010 | 30.0 | 2.5 | 5.60 |
| | Betamethasone-21-thio-propionate-17-propionate | 0.0013 | 231 | 3.0 | 4.66 |

| | Studied product | Anti-inflammatory activity | | Systemic activity | |
|---|---|---|---|---|---|
| | | $EC_{50}$ % p/v | Activity/ref. 21 act. hydro | $ED_{50}$ mg/kg/d$^{-1}$ | Activity/ref. 21 act. hydro |
| Comparison products | Dexamethasone-21-thio-t-butylacetate-17-acetate | 0.0092 | 32.6 | 3.0 | 4.67 |
| | Beclomethasone-21-thiopropionate-17-propionate | 0.0175 | 17.1 | 19 | 0.74 |
| Products of the invention | Example 1: Hydrocortisone-21-thioacetate-17-butyrate | 0.0082 | 36.6 | 350 | 0.04 |
| | Example 2: Hydrocortisone-21-thiopropionate-17-butyrate | 0.021 | 14.3 | >1450 | <0.0096 |

II.2. Utilizing the results

The results given in table I make it possible to determine a ratio:

local anti-inflammatory activity
systemic activity

The value of this ratio indicates the dissociation of the activities and is inversely proportional to the size of the dissociation, i.e. the lower this value, the greater the dissociation.

This value was calculated on the basis of the expression:

$$R = \frac{EC_{50} \text{ local anti-inflammatory activity}}{ED_{50} \text{ systemic activity}}$$

A comparison with hydrocortisone-21-acetate is also given in the following table II.

TABLE II

| Ref | Studied product | R | R hydrocortisone-21-acetate / R studied product |
|---|---|---|---|
| Comparison products | Hydrocortisone-21-acetate | 214 | 1 |
| | Hydrocortisone-21-propionate-17-butyrate | 6.52 | 32.8 |
| | Prednisolone-21-acetate-17-valerate | 2.0 | 107.0 |
| | Hydrocortisone-21-thiopivalate | 6.90 | 31.0 |
| | Prednisolone-21-thioacetate-17-valerate | 1.38 | 155 |
| | 6-α-methylprednisolone-21-thioacetate- | 116.3 | 1.85 |

TABLE II-continued

| Ref | Studied product | R | R hydrocortisone-21-acetate / R studied product |
|---|---|---|---|
| | 17-valerate | | |
| | Betamethasone-21-thiopropionate-17-acetate | 50.0 | 4.30 |
| | Betamethasone-21-thioacetate-17-propionate | 40.0 | 5.35 |
| | Betamethasone-21-thiopropionate-17-propionate | 4.33 | 49.40 |
| | Dexamethasone-21-thio-t-butylacetate-17-acetate | 30.7 | 7.0 |
| | Beclomethasone-21-thiopropionate-17-propionate | 9.21 | 23.20 |
| Products of the invention | Example 1: Hydrocortisone-21-thioacetate-17-butyrate | 0.23 | 930 |
| | Example 2: Hydrocortisone-21-thiopropionate-17-butyrate | 0.14 | 1528 |

In general terms, the derivatives according to the invention reveal an interesting anti-inflammatory activity. Overall, the value of this activity is comparable to that of 21-thio-17-oxo-diesters of steroids used as the comparison substance and in particular for similar derivatives in the betamethasone, beclomethasone and dexamethasone series, which are considered as basic substances with a powerful activity.

However, the products according to the invention have an activity which is well below that of the studied oxygenated diesters.

Apart from hydrocortisone-21-thiopivalate, the products according to the invention surprisingly reveal a spectacular reduction in the systemic activity compared with the studied comparison products. Thus, in this test, it was found that the product of example 1, which gives the least satisfactory results of the two selected products, still has an activity 6 times lower than that of the prednisolone-21-thioacetate-17-valerate, which is the best in the series of comparison products.

Without doubt, the dissociation ratio of these activities, reveals the superiority of the products according to the invention compared with the other products studied. In the particular case of the product of example 2, the dissociation of the activities is more than 45 times better than that of its homologue, hydrocortisone-21-propionate-17-butyrate, the product according to French Patent No. 2,421,480, whilst in the prednisolone series, 21-thioacetate,17-valerate only has a dissociation which is approximately 1,5 times better than that of its oxygenated homologue (comparison of the second and fourth comparison products).

These surprising properties reveal the remarkable superiority of the products according to the invention and their interest as anti-inflammatory agents.

The products according to the invention can be administered by the general and local route in the form of pharmaceutical compositions suitable for their use. In the same way, these properties make it possible to envisage active agent quantities of 0.1 to 100 mg per dosage unit. The active agent can be administered daily in quantities between 0.1 and 500 mg, as a function of the nature and location of the ailment to be treated.

For administration by the general route, solid or liquid forms can be used, such as injectable or non-injectable solutions and suspensions, as well as tablets, capsules, gelatin-coated pills and granules.

For the local route, the preferred compositions are ointments, salves, creams, emulsions, lotions, drops, enemas, suppositories, ovules, instillations and aerosols.

Obviously, these pharmaceutical compositions may also contain other active principles compatible with the products according to the invention such as, and without this list being limitative, preservatives, bacteriostatics, antibiotics, antimycotics and local anesthetics.

In the case of pharmaceutical compositions in which the products according to the invention are in the suspended state, it is advantageous to use active principles in micronized form, with an average grain size of 5 microns. In certain special cases, particularly in aerosols, it is necessary to use the active principle in micronized form with a grain size of approximately 2 microns.

These pharmaceutical compositions are prepared in accordance with well known formulations and conditions, whilst respecting the standards of the pharmaceutical industry.

The properties of the products according to the present invention are useful in the treatment of inflammatory ailments having the most varied causes.

Their action is particularly useful in the treatment of inflammation of the mucous membranes in the ORL region, as well as the bronchi, particularly in the treatment of asthma.

They can also be used for the treatment of skin diseases, such as eczema and psoriasis. Moreover, their action is beneficial in the treatment of rectal ailments and ailments of the colon.

The products according to the present invention can also be used for the treatment of internal ailments having various causes, such as arthritis, polyarthritis and various allergic diseases.

We claim:

1. A method for treating an inflammatory ailment comprising administering to a person suffering from said inflammatory ailment an amount effective to treat said ailment of a member selected form the group consisting of 3,20-dione-11$\beta$-hydroxypregn-4-ene-21-thioacetate-17-butyrate and 3,20-dione-11$\beta$-hydroxypregn-4-ene-21-thiopropionate-17-butyrate.

2. The method of claim 1 wherein said member is administered daily in an amount ranging between 0.1 and 500 mg.

3. The method of claim 1 wherein said member is administered in an amount of 0.1 to 100 mg per dosage unit.

* * * * *